United States Patent [19]

Watanabe et al.

[11] Patent Number: 4,701,613
[45] Date of Patent: Oct. 20, 1987

[54] ELECTRO-OPTICAL RAIN DETECTOR FOR WINDSHIELDS

[75] Inventors: Takashi Watanabe; Nobuo Tsuda, both of Kariya; Inao Tomikawa, Toyota, all of Japan

[73] Assignee: Nippondenso Co., Ltd., Kariya, Japan

[21] Appl. No.: 796,767

[22] Filed: Nov. 12, 1985

[30] Foreign Application Priority Data

Nov. 9, 1984 [JP] Japan .................. 59-237184

[51] Int. Cl.⁴ .............................. H01J 5/16
[52] U.S. Cl. .................. 250/227; 250/577; 340/602
[58] Field of Search ........... 250/577, 227; 340/602; 350/96.19; 73/293

[56] References Cited

U.S. PATENT DOCUMENTS

| 3,674,335 | 7/1972 | Ashkin et al. | 350/96.19 |
| 4,518,259 | 5/1985 | Ward | 250/227 X |
| 4,589,771 | 5/1986 | Watanabe et al. | 356/38 |

FOREIGN PATENT DOCUMENTS

| 51-5141 | 1/1976 | Japan . | |
| 0085944 | 5/1984 | Japan | 340/602 |
| 0084141 | 5/1984 | Japan | 340/602 |
| 59-152449 | 10/1984 | Japan . | |
| 59-152446 | 10/1984 | Japan . | |
| 1242621 | 8/1971 | United Kingdom . | |

Primary Examiner—Eugene R. LaRoche
Assistant Examiner—David Mis
Attorney, Agent, or Firm—Cushman, Darby & Cushman

[57] ABSTRACT

An electro-optical liquid detector assembly comprises a support block having a flat front surface attached to the internal surface of a wind-shield and being formed therein with a pair of inclined bores opening toward the internal surface of the wind-shield, a transparent flat plate contained within the support block and fixed to the support block to form a common flat front surface with the support block, the transparent flat plate being formed in its rear surface with a pair of spaced v-grooved portions which are opposed to the inclined bores, a light emitting element disposed within one of the inclined bores to emit a beam of light into the wind-shield through one of the v-grooved portions of the flat plate so as to cause internal reflection of the beam between the external and internal surfaces of the wind-shield, and a light receiving element disposed within the other inclined bore to receive the incident beam reflected by the external surface of the wind-shield through the other v-grooved portion of the flat plate so as to produce an electric signal indicative of an amount of the incident beam.

8 Claims, 2 Drawing Figures

ELECTRO-OPTICAL RAIN DETECTOR FOR WINDSHIELDS

BACKGROUND OF THE INVENTION

The present invention relates to an automatic control apparatus for wind-shield wipers, and more particularly to an electro-optical liquid detector assembly for the automatic control apparatus which is adapted to electro-optically detect an adherence condition of liquid such as raindrops on the external surface of a wind-shield of wheeled vehicles, airplanes, ships or the like so as to produce an electric control signal necessary for automatic control of a wind-shield wiper in dependence upon a result of the detection.

In a Japanese Early Publication for Utility Model No. 51-5141, there has been proposed an electro-optical detector assembly which comprises a reflection plate attached to the internal surface of a wind-shield at a portion where the external surface of the wind-shield is wiped by a wiper blade, a pair of spaced prisms attached to the internal surface of the wind-shield at opposite sides of the reflection plate, a light emitting element arranged to emit a beam of light into the wind-shield through one of the prisms so as to cause multiple internal reflection of the beam between the external surface of the wind-shield and the reflection plate, and a light receiving element arranged to receive the incident beam reflected by the external surface of the wind-shield through the other prism. In such a conventional liquid detector assembly, the prisms each are, in general, made of transparent synthetic resin such as poly-carbonate, acrylate or the like. In making of such a prism of transparent synthetic resin, a time difference will occur in coagulation of the respective portions of the prism. For this reason, the prism is formed thereon with uneven surfaces and therein with air bubbles. Such uneven surfaces on the prism and/or air bubbles in the prism will cause turbulent reflection and irregular refraction of the incident beam, resulting in malfunction of the light receiving element. Particularly, this problem will increase in the case that a large size prism is adapted to expand the region for detection of liquid adhered to the external surface of the wind-shield.

SUMMARY OF THE INVENTION

It is, therefore, a primary object of the present invention to provide an electro-optical liquid detector assembly capable of expanding the region for detection of liquid adhered to the external surface of the wind-shield in a simple construction without causing the problems described above.

According to the present invention there is provided an electro-optical liquid detector assembly which comprises a support block having a flat front surface attached to the internal surface of a wind-shield at a portion where the external surface of the wind-shield is wiped by a wiper blade, the support block being formed therein with a pair of spaced inclined bores opening toward the internal surface of the wind-shield, a transparent flat plate contained within the support block and fixed to the support block to form a common flat front surface with the support block, the transparent flat plate being formed in its rear surface with a pair of spaced v-grooved portions which are opposed to the inclined bores in the support block, a light emitting element disposed within one of the inclined bores in the support block to emit a beam of light into the wind-shield through one of the v-grooved portions of the transparent flat plate so as to cause internal reflection of the beam between the internal and external surfaces of the wind-shield, and a light receiving element disposed within the other inclined bore in the support block to receive the incidend beam reflected by the external surface of the wind-shield through the other v-grooved portion of the transparent flat plate so as to produce an electric signal indicative of an amount of the incident beam.

BRIEF DESCRIPTION OF THE DRAWINGS

Additional objects, features and advantages of the present invention will become more readily apparent from the following detailed description of preferred embodiments thereof when taken together with the appended drawings, in which.

DETAILED DESCRIPTION OF THE PREFERRED EMBODIMENTS

Figure 1:
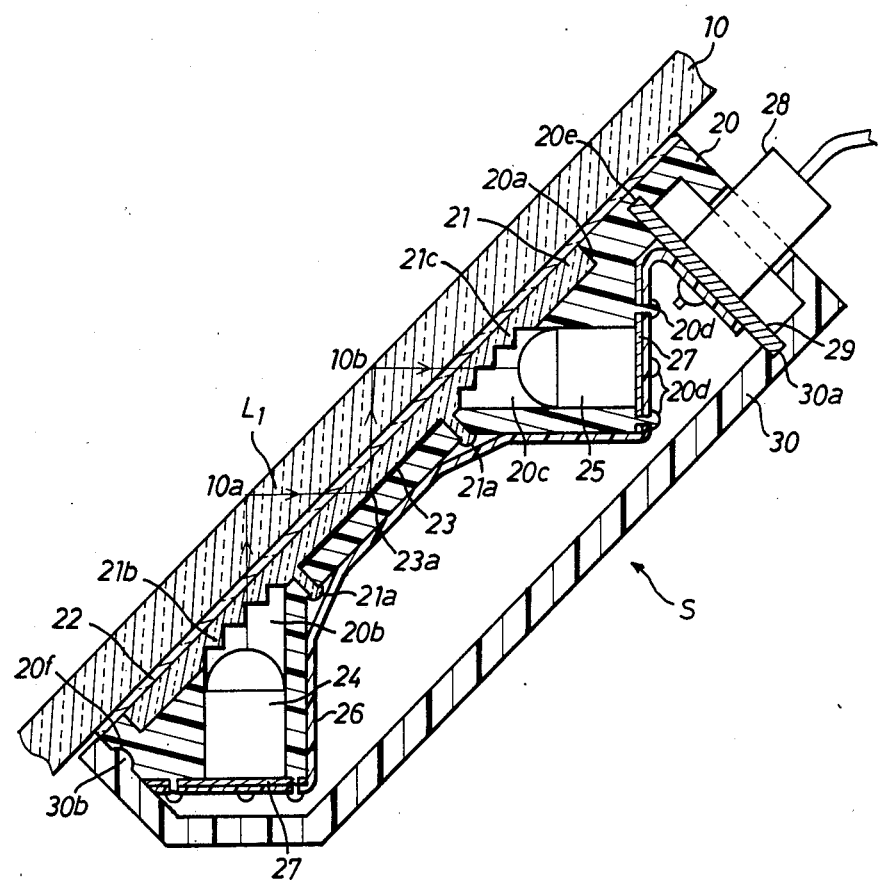
FIG. 1 is a sectional view of an embodiment of an electro-optical liquid detector assembly in accordance with the present invention.

Referring to FIG. 1 of the drawings, there is illustrated an electro-optical liquid detector assembly S in accordance with the present invention which is attached to the internal surface of a front wind-shield or front glass 10 adjacent an inside roof panel of a vehicle compartment. The liquid detector assembly S comprises a support block 20 of synthetic resin having a flat front surface, and a transparent flat plate 21 contained within a recess 20a in the support block 20 and welded at 21a to the support block 20 to form a common flat front surface with the support block 20. The support block 20 and transparent flat plate 21 are positioned at a portion of front glass 10 where the external surface of front glass 10 is wiped by a wiper blade (not shown) of an electrically operated wind-shield wiper mechanism for the vehicle, and they are adhered to the internal surface of front glass 10 by means of a transparent adhesive 22 coated to the common flat front surface thereof.

A reflection thin plate 23 is secured to the central portion of the rear surface of transparent flat plate 21 to effect total reflection of near infrared rays emitted into the front glass 10 through the transparent flat plate 21. The support block 20 is further formed therein with a pair of spaced inclined bores 20b and 20c which are arranged symmetrically with respect to the reflection thin plate 23. A light emitting element 24 is disposed within the bore 20b, while a light receiving element 25 is disposed within the bore 20c. In such an arrangement of the electro-optical elements 24, 25, an angle of the light emission axis of element 24 to a normal at an intersect point 10a on the external surface of front glass 10 is determined to be a value between critical angles respectively in relation to the outside air on the external surface of front glass 10 and in relation to an amount of liquid such as raindrops on the external surface of front glass 10. This means that when any liquid does not exist on the external surface of front glass 10, the near infrared rays emitted from element 24 into the front glass 10 through transparent flat plate 21 are totally reflected by the external surface of glass 10 and that when an amount of liquid is adhered to the external surface of front glass 10 at intersect point 10a, the amount of near infrared rays reflected by the external surface of glass 10 is decreased. Meanwhile, the light receiving element 25 is arranged within the support block 20 in such a manner that the light receiving axis of element 25 coincides with the incident near infrared rays reflected by the external surface of glass 10 at an intersect point 10b after multiple internal reflection between the external surface of glass 10 and the reflection thin plate 23.

The rear surface of support block 20 is covered by a flexible printed board 26 to which the electro-optical elements 24, 25 and their associated electric parts are soldered. The flexible printed board 26 is welded at 20d to the support block 20 and is reinforced by reinforcement plates 27 of insulation material fixed thereto to firmly support the electro-optical elements 24, 25 in place. The flexible printed board 26 is connected to an electric control circuit (not shown) for the wiper mechanism through a connector 28 which is soldered to an upper folded portion of printed board 26 through a retainer plate 29 of insulation material engaged at its one end with a groove 20e in the support block 20. A cover member 30 is coupled over the support block 20 to protect the electric parts mounted on the printed board 26 and is fixed in place by engagement with a recess 20f of support block 20 at its internal projection 30b and engagement with the other end of retainer plate 29 at its internal groove 30a.

The transparent flat plate 21 is made of transparent synthetic resin such as transparent acrylate, poly-carbonate or the like which has substantially the same refractive index as that of the front glass 10 to the near infrared rays. The transparent flat plate 21 is colored to permit only the near infrared rays passing therethrough and has a thickness of 2 mm-4 mm. The transparent flat plate 21 is formed with v-grooved portions 21b and 21c which are opposed to the electro-optical elements 24 and 25, respectively. The v-grooved portion 21b has a plurality of elongated parallel oblique planes arranged perpendicular to the light emission axis of element 24 and has a plurality of elongated parallel oblique planes arranged in parallel with the light emission axis of element 24. With the above arrangement, the v-grooved portion 21b of transparent flat plate 21 permits only the near infrared rays entering into the front glass 10 from element 24 through its parallel oblique planes perpendicular to the light emission axis of element 24. Thus, all the near infrared rays from element 24 are directed to the front glass 10 through the v-grooved portion 21b of transparent flat plate 21 without causing any reflection or refraction.

The v-groove portion 21c of transparent flat plate 21 has a plurality of elongated parallel oblique planes arranged perpendicular to the light receiving axis of element 25 and has a plurality of elongated parallel oblique planes arranged in parallel with the light receiving axis of element 25. With this arrangement, the v-grooved portion 21c of transparent flat plate 21 permits only the incident near infrared rays entering into the light receiving element 25 through its parallel oblique planes perpendicular to the light receiving axis of element 25. Thus, all the incident near infrared rays reflected by the external surface of front glass 10 at intersect point 10b are directed to the light receiving element 25 through the v-grooved portion 21c of transparent flat plate 21 without causing any reflection or refraction.

The light emitting element 24 includes an infrared ray light emitting diode contained within the bore 20b, and a lens coupled with the diode to convert near infrared rays emitted from the diode into parallel near infrared rays $L_1$. The light receiving element 25 includes an infrared ray light photodiode contained within the bore 20c, and a focusing lens coupled with the photodiode to forcalize the incident parallel near infrared rays to the photodiode.

In manufacture of the liquid detector assembly S, the component parts are assembled as follows, (1) The electro-optical elements 24, 25 and connector 28 are soldered to the flexible printed board 26 respectively through the reinforcement plates 27 and retainer plate 29.

(2) The reflection thin plate 23 is previously secured to the transparent flat plate 21. The transparent flat plate 21 is coupled within the recess 20a of support block 20 and welded at 21a to the support block 20.

(3) The flexible printed board 26 is coupled over the support block 20 and welded at 20d to the support block 20 in such a manner that the electro-optical elements 24, 25 are respectively coupled within the bores 20b, 20c in support block 20 and that the retainer plate 29 is engaged with the groove 20e of support block 20.

(4) The cover member 30 is coupled over the support block 20 and fixed in place by engagement with the retainer plate 29 at its internal groove 30a and engagement with the recess 20f of support block 20 at its internal projection 30b.

When the liquid detector assembly S is attached to the internal surface of front glass 10, the cover member 30 is removed from the support block 20. Thereafter, the support block 20 and transparent flat plate 21 are uniformly coated at their front flat surfaces with the transparent adhesive and adhered to the internal surface of front glass 10. After coagulation of the adhesive, the cover member 30 is detachably coupled with the support block 20 to facilitate repair of the component parts in the liquid detector assembly S.

In the liquid detector assembly S, the v-grooved portion 21b of transparent flat plate 21 permits the parallel near infrared rays $L_1$ entering into the front glass 10 from the light emitting element 24 through its parallel oblique planes perpendicular to the light emission axis of element 24. The near infrared rays $L_1$ are reflected by the external surface of glass 10 at intersect point 10a to propagate to the reflection thin plate 23 through the transparent adhesive layer 22 and flat plate 21, and subsequently the incident near infrared rays $L_1$ are reflected by the reflection thin plate 23 at an intersect point 23a to propagate to the external surface of glass 10 through the transparent flat plate 21 and adhesive layer 22. The incident near infrared rays $L_1$ are further reflected by the external surface of glass 10 at intersect point 10b to propagate to the light receiving element 25 through the transparent adhesive layer 22 and flat plate 21. Thus, the v-grooved portion 21c of transparent flat plate 21 permits the incident near infrared rays $L_1$ entering into the light receiving element 25 through its parallel oblique planes perpendicular to the light receiving axis of element 25.

When any liquid does not exist on the external surface of front glass 10 in a region between the intersect points 10a and 10b, the incident near infrared rays are totally reflected by the external surface of glass 10. When received the totally reflected rays, the photodiode of element 25 is energized to produce an electric signal indicative of an amount of the reflected incident near infrared rays. Thus, the electric signal is applied to the electric control circuit through the connector 28 to produce an electric control signal necessary for automatic control of the wind-shield wiper mechanism. When an amount of liquid such as raindrops is adhered to the external surface of front glass 10 in the region, a portion of the incident near infrared rays propagates into the outside air through the adhered liquid to decrease the amount of incident near infrared rays applied to the photodiode of element 25. Then, the photodiode of element 25 produces an electric singal indicative of the decreased amount of incident near infrared rays, and the electric control circuit produces an electric control signal for activating the wind-shield wiper mechanism in accordance with a value of the electric signal from the photodiode of element 25.

Figure 2:
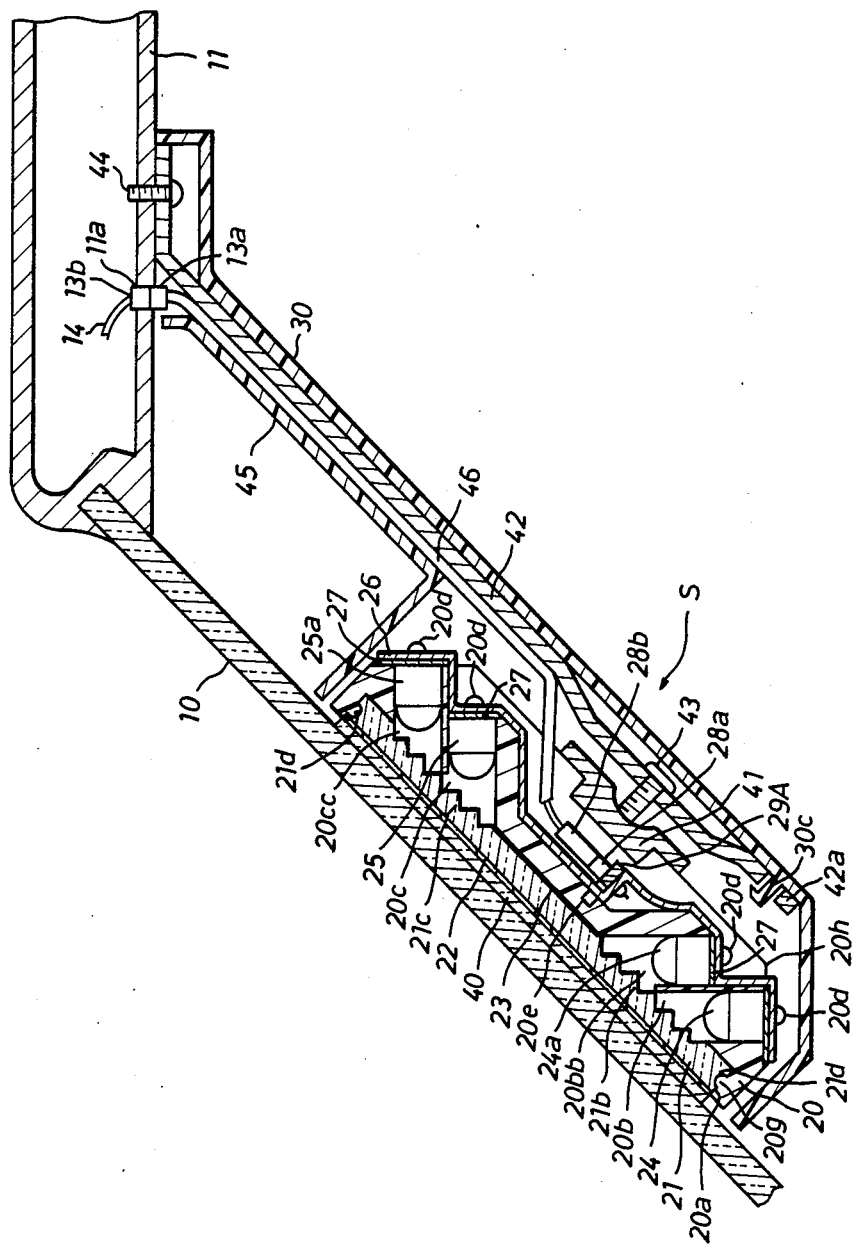
FIG. 2 is a sectional view of a modification of the electro-optical liquid detector assembly shown in FIG. 1.

A modification of the liquid detector assembly S is illustrated in FIG. 2, wherein the same component parts as those in the above-described embodiment are indicated by the same reference numerals. In this modification, the transparent flat plate 21 is formed at its opposite ends with a pair of recesses 21d which are engaged with internal projections 20g of the support block 20, and a transparent elastic flat plate 40 is adhered to the front surface of transparent flat plate 21 by means of the transparent adhesive 22 to resiliently attach the liquid detector assembly S to the internal surface of front glass 10. The transparent elastic flat plate 40 is made of transparent silicon rubber which has substantially the same refractive index as that of the front glass 10 to the near infrared rays. The thickness of elastic flat plate 40 is determined to be 1 mm-3 mm. The support block 20 is further formed at its opposite sides with a pair of laterally spaced ribs 20h for support of a rectangular lateral thrust plate 41. The thrust plate 41 is engaged at its opposite ends with the laterally spaced ribs 20h of support block 20 and pressed toward the front glass 10 by means of an adjusting screw 43 threaded into a support frame 42. The support frame 42 is secured at its upper end to a front portion of an inside roof panel 11 by means of a screw 44 to press the liquid detector assembly S into contact with the internal surface of front glass 10. A cover member 30 is coupled over the support frame 42 and fixed in place by engagement with the lower end portion 42a of support frame 42 at its internal hooks 30c. An inside cover member 45 is further fixed to the support frame 42 in an appropriate manner.

The support block 20 is further formed therein with a pair of inclined bores 20bb and 20cc which are arranged in parallel with the respective inclined bores 20b and 20c and opposed to the respective v-grooved portions 21b and 21c of transparent flat plate 21. Disposed within the inclined bores 20bb and 20cc are a light emitting element 24a and a light receiving element 25a, respectively. The electro-optical elements 24a and 25a are secured to the flexible printed board 26 in the same manner as the electro-optical elements 24 and 25 shown in FIG. 1. In this modification, the flexible printed board 26 is disposed between the laterally spaced ribs 20h of support block 20 and welded at 20d to the support block 20 through the respective reinforcement plates 27. Thus, the electric parts on printed board 26 are contained within a space between the ribs 20h of support block 20. A retainer plate 29A is secured to a folded portion of printed board 26 and engaged with a groove 20e in support block 20 to retain the printed board 26 in place. A connector 28a is soldered to a connection terminal of printed board 26 through retainer plate 29A and connected to a lower socket 28b of a leading wire 46 which extends along the support frame 42 toward the inside roof panel 11. An upper socket 13a of leading wire 46 is connected to a connector 13b which is fixed at 11a to the inside roof panel 11 and connected to the electric control circuit for the wiper mechanism through a leading wire 14. The other component parts and construction of the modification are substantially the same as those in the liquid detector assembly S shown in FIG. 1.

In manufacture of the modified liquid detector assembly, the component parts are assembled as follows.

(1) The electro-optical elements 24, 24a, 25, 25a and connector 28a are soldered to the flexible printed board 26 respectively through the reinfocement plates 27 and retainer plate 29A.

(2) The transparent elastic flat plate 40 is adhered to the front surface of transparent flat plate 21 by means of the transparent adhesive.

(3) The transparent flat plate 21 is coupled within the recess 20a of support block 20 and fixed in place by engagement with the internal projections 20g of support block 20 at its recesses 21d.

(4) The flexible printed board 26 is coupled over the support block 20 and welded at 20d to the support block 20 in such a manner that the electro-optical elements 24, 24a, 25, 25a are respectively disposed within the bores 20b, 20bb, 20c, 20cc in support block 20 and that the retainer plate 29A is engaged with the groove 20e of support block 20.

(5) The lower socket 28b of leading wire 46 is connected to the connector 28a.

(6) The lateral thrust plate 41 is engaged with the laterally spaced ribs 20h of support block 20.

(7) The adjusting screw 43 is threaded into the support frame 42. Thereafter, the cover members 30 and 45 are assembled with the support frame 42.

When the modified liquid detector assembly is attached to the internal surface of front glass 10, the cover member 30 is removed from the support frame 42, and the upper socket 13a of leading wire 46 is connected to the connector 13b. Thereafter, the support frame 42 is fixed at its upper end to the inside roof panel 11 by means of the screw 44, and the adjusting screw 43 is fastened to press the support block 20 through the lateral thrust plate 42 toward the internal surface of front glass 10 and fixedly retain it in place. Thus, the transparent elastic flat plate 40 is uniformly pressed into contact with the internal surface of front glass 10 without causing any air gaps. Finally, the cover member 30 is detachably engaged with the support frame 42 to facilitate repair of the component parts in the liquid detector assembly.

Having now fully set forth both structure and function of preferred embodiments of the concept underlying the present invention, various other embodiments as well as certain variations and modifications of the embodiments herein shown and described will obviously occur to those skilled in the art upon becoming familiar with said underlying concept. It is to be understood, therefore, that within the scope of the appended claims, the invention may be practiced otherwise than as specifically set forth herein.

What is claimed is:

1. An electro-optical rain detector assembly comprising:
   a support block having a flat front surface attached to the internal surface of a wind-shield at a portion where the external surface of said wind-shield is wiped by a wiper blade, said support block being formed therein with a pair of spaced inclined bores opening toward the internal surface of said wind-shield;

a transparent flat plate fixedly coupled within a corresponding recess in said support block to form a common flat front surface with said support block, said transparent flat plate being formed in a rear surface thereof with a pair of spaced v-grooved portions which are opposed to the inclined bores in said support block;

a light emitting element disposed within one of the inclined bores in said support block to emit a beam of light into said wind-shield through one of the v-grooved portions of said transparent flat plate so as to cause internal reflection of the beam between the external and internal surfaces of said wind-shield; and a light receiving element disposed within the other inclined bore in said support block to receive the incident beam reflected by the external surface of said wind-shield through the other v-grooved portion of said transparent flat plate so as to produce an electric signal indicative of an amount of the incident beam;

one of said v-grooved portions having a plurality of elongated parallel oblique planar regions disposed perpendicular to the light emission axis of said light emitting element and a plurality of elongated parallel oblique planar regions disposed in parallel with said light emission axis, and the other of said v-grooved portions having a plurality of elongated parallel oblique planar regions disposed perpendicular to the light receiving axis of said light receiving element and a plurality of elongated parallel oblique planar regions disposed in parallel with said light receiving axis.

2. An electro-optical rain detector assembly as claimed in claim 1, wherein a reflection thin plate is secured to the rear surface of said transparent flat plate located between said v-grooved portions to effect multiple internal reflection of the beam in said wind-shield.

3. An electro-optical rain detector assembly as claimed in claim 1, wherein said support block and transparent flat plate are adhered to the internal surface of said wind-shield at the common flat front surface thereof.

4. An electro-optical rain detector assembly as claimed in claim 1, wherein said transparent flat plate is made of transparent synthetic resin.

5. An electro-optical rain detector assembly for detecting an adhereence condition of raindrops on the external surface of a wind-shield, comprising:

a support block having a flat front surface attached to the internal surface of said wind-shield at a portion where the external surface of said wind-shield is wiped by a wiper blade, said support block being formed therein with a pair of spaced inclined bores opening toward the internal surface of said wind-shield;

a transparent flat plate fixedly coupled within a corresponding recess in said support block to form a common flat front surface with said support block, said transparent flat plate being formed in a rear surface thereof with a pair of spaced v-grooved portions which are opposed to the inclined bores in said support block;

a transparent elastic flat plate adhered to the common flat front surface of said transparent flat plate;

at least one light emitting element disposed within one of the inclined bores in said support block to emit a beam of light into said wind-shield through one of said v-grooved portions of said transparent flat plate so as to cause internal reflection of the beam between the external and internal surfaces of said wind-shield;

at least one light receiving element disposed within the other inclined bore in said support block to receive the incident beam reflected by the external surface of said wind-shield through the other v-grooved portion of said transparent flat plate so as to produce an electric signal indicative of an amount of the incident beam; and a frame member fixedly mounted on a stationary structure adjacent said wind-shield to support said support block thereon and press said support block toward the internal surface of said wind-shield through said elastic flat plate.

6. An electro-optical rain detector assembly as claimed in claim 5, wherein:

said at least one light emitting element comprises a plurality of light emitting elements disposed in parallel within one of the inclined bores in said support block to emit plural beams of light into said wind-shield through the one of said v-grooved portions; and said at least one light receiving element comprises a plurality of light receiving elements disposed in parallel within the other inclined bore in said support block to receive the incident beams reflected by the external surface of said wind-shield through the other v-grooved portion.

7. An electro-optical rain detector assembly as claimed in claim 5, further comprising:

a thrust plate engaged with a rear portion of said support block and pressed toward said wind-shield by means of an adjusting screw threaded into said frame member.

8. An electro-optical rain detector assembly as claimed in claim 5, wherein:

said transparent flat plate is made of transparent synthetic resin, and said elastic flat plate is made of transparent silicone rubber.

* * * * *